(12) United States Patent
Teitelbaum

(10) Patent No.: US 6,607,482 B1
(45) Date of Patent: Aug. 19, 2003

(54) AUTOMATED QUESTIONNAIRE FOR ASSISTING IN THE DIAGNOSIS AND TREATMENT OF MEDICAL PROBLEMS AND FOR DATA GATHERING, ANALYSIS AND ORGANIZATION TO MAKE A COMPLETE MEDICAL HISTORY AND ILLNESS RECORD

(76) Inventor: Jacob Teitelbaum, 466 Forelands Rd., Annapolis, MD (US) 21401

( * ) Notice: Subject to any disclaimer, the term of this patent is extended or adjusted under 35 U.S.C. 154(b) by 0 days.

(21) Appl. No.: 09/722,493

(22) Filed: Nov. 28, 2000

(51) Int. Cl.⁷ .................................................. A61B 5/00
(52) U.S. Cl. ...................................... 600/300; 128/920
(58) Field of Search ............................ 600/300, 301; 128/903.904, 920–925; 705/2–4; 706/924; 434/262

(56) References Cited

U.S. PATENT DOCUMENTS

| | | |
|---|---|---|
| 5,572,421 A | 11/1996 | Altman et al. |
| 5,594,638 A | 1/1997 | Iliff |
| 5,802,495 A | 9/1998 | Goltra |
| 5,823,948 A | 10/1998 | Ross, Jr. et al. |
| 5,823,949 A * | 10/1998 | Goltra .......................... 600/300 |
| 5,835,900 A | 11/1998 | Fagg, III et al. |
| 5,839,438 A | 11/1998 | Graettinger et al. |
| 5,935,060 A | 8/1999 | Iliff |
| 6,022,315 A | 2/2000 | Iliff |
| 6,047,259 A | 4/2000 | Campbell et al. |
| 6,053,866 A | 4/2000 | McLeod |
| 6,063,026 A | 5/2000 | Schauss et al. |
| 6,071,236 A | 6/2000 | Iliff |
| 6,113,540 A * | 9/2000 | Iliff .............................. 600/300 |
| 6,120,440 A | 9/2000 | Goknar |
| 6,126,596 A | 10/2000 | Freedman |
| 6,290,646 B1 * | 9/2001 | Cosentno et al. ........... 600/300 |

OTHER PUBLICATIONS

Jacob Teitelbaum, MD; *From Fatigued To Fantastic*; 1996.

* cited by examiner

Primary Examiner—Max F. Hindenburg
Assistant Examiner—Michael C Astorino

(57) ABSTRACT

A method and system for assisting in the diagnosis of a patient's symptoms. The method and system gather information regarding the patient's symptoms and past medical history. A review of the patient's systems are also made systematically in order to find the root of the patient's symptoms instead of merely finding a temporary cure alleviating symptoms without curing the symptoms. The method and system also reviews a patient's psychological profile and an analysis of a patient's exposure to mold. Finally, a diagnosis is made by assigning point values to the information gathered creating a diagnosis based on the point values. In order better assess the information that is gathered and the diagnosis that is created, the information is organized into a formatting document that organizes everything into a more sensible and readable format for one to analyze. This instrument aids the physician by 1) eliciting the needed medical information for the doctor, 2) analyzing the information to determine needed testing, probable diagnosis and needed treatments, 3) creating a complete medical record in the proper format for physicians and 4) supplying detailed teaching information to the patient about their illness and treatments. Thus, the present invention can be used as a computerized physician/diagnosis/teaching program by both patients and doctors.

17 Claims, 8 Drawing Sheets

FIG.2

[ Close Without Saving ] [ Save and Mark Complete ] [ Save and Mark Incomplete ] [ Submit To ] ▷

Questionnaire Section One for jacob e6 teitelbaum

Use TAB key to move the cursor to the next question.

If unsure, it is OK to give your best guess or leave blank. Most people won't know all of the answers.

Please describe briefly (in one sentence) what your main problem(s) are (You will be able to describe things at length later in the questionnaire).

| I'm tired, achy and brain foggy |

How long have you been fatigued or how long have you been in pain? | 25 years |

What was the approximate date or time of onset? | 1975 |

How much has fatigue decreased your function?

| 75% |

Have you been diagnosed by a physician (MD or DO) with *(please mark all that apply)*
☑ Fibromyalgia
☑ Chronic Fatigue If so, when were you first diagnosed?
    | 1984 |

Symptoms began: ⦿ Suddenly ○ Gradually

What symptoms presented at onset?

| flu-mono like. tired, achy and had to stay in bed till noon each day |

What stresses were occurring in your life when the disease began?

| Med school and family and political stresses |

Did you receive any vaccines within three months before onset of symptoms?
○ Yes
⦿ No If yes, list the vaccines and note how soon after which vaccination the symptoms appeared:

FIG. 3

[Close Without Saving] [Save and Mark Complete] [Save and Mark Incomplete]

Questionnaire Section Two for jacob e6 teitelbaum

Please note any of the treatments you are taking or have taken (Rx means by prescription only)

| a | Treatment Use | Current Dose | Treatment Effect |
|---|---|---|---|
| Treatment | If you have ever taken this treatment, check: | What dose are you currently taking? | Check the effect of this treatment (can select more than one): |
| Rx-Elavil (Amitriptyline) | ☐ On it now<br>☑ Took in past | [25] mg<br>[3] x a day<br>or<br>☐ As Needed | ☐ Helps/Helped<br>☐ Doesn't Help/Didn't Help<br>☐ Don't Know<br>☑ Severe Side Effects<br>☐ Other |
| Rx-Flexeril (Cyclobenzaprine) | ☐ On it now<br>☐ Took in past | [ ] mg<br>[ ] x a day<br>or<br>☐ As Needed | ☐ Helps/Helped<br>☐ Doesn't Help/Didn't Help<br>☐ Don't Know<br>☐ Severe Side Effects<br>☐ Other |
| Rx-Desyrel (Trazodone) | ☐ On it now<br>☑ Took in past | [25-5] mg<br>[ ] x a day<br>or<br>☐ As Needed | ☑ Helps/Helped<br>☐ Doesn't Help/Didn't Help<br>☐ Don't Know<br>☐ Severe Side Effects<br>☐ Other |
| Rx-Ambien (Zolpidem) | ☐ On it now<br>☑ Took in past | [10] mg<br>[1] x a day<br>or<br>☐ As Needed | ☑ Helps/Helped<br>☐ Doesn't Help/Didn't Help<br>☐ Don't Know<br>☐ Severe Side Effects<br>☐ Other |
| a | Treatment Use | Current Dose | Treatment Effect |
| Rx-Xanax (Aprazolam) | ☐ On it now<br>☐ Took in past | [ ] mg<br>[ ] x a day<br>or<br>☐ As Needed | ☐ Helps/Helped<br>☐ Doesn't Help/Didn't Help<br>☐ Don't Know<br>☐ Severe Side Effects<br>☐ Other |
| Rx-Klonopin (Clonazepam) | ☐ On it now<br>☐ Took in past | [ ] mg<br>[ ] x a day<br>or<br>☐ As Needed | ☐ Helps/Helped<br>☐ Doesn't Help/Didn't Help<br>☐ Don't Know<br>☐ Severe Side Effects<br>☐ Other |

FIG. 4

[Close Without Saving] [Save and Mark Complete] [Save and Mark Incomplete]

04/21/52~MD~Male~Married~5~amy19,dave15,shannon21,brittany17,kelly13~pcn~sugar~No~^~^~48~I'm tired,achy and brain foggy~25 years~1975~75%~Suddenly~flu-mono like. tired,achy and had to stay in bed till noon each day~Med school and family and political stresses
~Yes~SISTER~7~110~0~45~35~^~^B10E0v0Q50

Questionnaire Section Three for jacob e6 teitelbaum

Use TAB key to move the cursor to the next question.

Symptom Checklist

*I. CFIDS Criteria*

Has your fatigue not been lifelong (i.e. you were not born severely tired) and not the result of ongoing exertion; and not substantially alleviated by rest; and your fatigue does result in substantial reduction in previous levels of occupation, education, social or personal activities?
◉ Yes ○ No Check the following symptoms if they have persisted or recurred during six or more consecutive months of illness and have not significantly predated the fatigue:

- ☑ Impairment in short-term memory or concentration severe enough to cause substantial reduction in previous levels of personal activity
- ☑ Sore throat
- ☑ Tender neck or axillary (armpit) lymph nodes
- ☑ Muscle pain
- ☐ Multijoint pain without joint swelling or redness
- ☐ Headaches of a new type or pattern or severity
- ☑ Unrefreshing sleep
- ☐ Post-exertional fatigue lasting more than 24 hours

*II. Fibromyalgia Criteria*

Have you had chronic widespread pain for more than three months in all four quadrants of the body (i.e. above and below the waist and on both sides of the body) and also axial pain (i.e. headache or pain around the spine or chest)?
◉ Yes ○ No What is the main symptom that made you decide to do this program?

| fatigue |
|---|

Please rate the following on a scale of 1 to 10:

| How is your energy?<br>(1=near dead; 10=excellent)<br>3 ▼ | How is your sleep?<br>(1=no sleep; 10=8 hours sleep no waking)<br>4 ▼ |
|---|---|
| How is your mental clarity?<br>(1=brain dead; 10=good clarity)<br>6 ▼ | How bad is your achiness?<br>(1=very severe pain; 10=pain free)<br>7 ▼ |

FIG.5

[Close Without Saving] [Save and Mark Complete] [Save and Mark Incomplete]

Questionnaire Section Four for jacob e6 teitelbaum

Use TAB key to move the cursor to the next question.

Beck Inventory

On this questionnaire are groups of statements. Please read each group of statements carefully. Then pick out the one statement in each group which best describes the way you have been feeling the past week, including today! Click the circle next to the number beside the statement you picked. If several statements in each group seem to apply equally as well, choose the one that seems closest. Be sure to read all the statements in each group before making your choice.

| | |
|---|---|
| A | ⊙ I do not feel sad<br>○ I do feel sad<br>○ I am sad all the time and can't snap out of it<br>○ I am so sad or unhappy that I can't stand it |
| B | ⊙ I am not particularly discouraged about the future<br>○ I feel discouraged about the future<br>○ I feel I have nothing to look forward to<br>○ I feel that the future is hopeless and that things cannot improve |
| C | ⊙ I do not feel like a failure<br>○ I feel I have failed more than the average person<br>○ As I look back on my life all I can see is a lot of failures<br>○ I feel I am a complete failure as a person |
| D | ⊙ I get as much satisfaction out of things as I used to<br>○ I don't enjoy things the way I used to<br>○ I don't get real satisfaction out of anything anymore<br>○ I am dissatisfied or bored with everything |
| E | ⊙ I don't feel particularly guilty<br>○ I feel guilty a good part of the time<br>○ I feel quite guilty most of the time<br>○ I feel guilty all the time |
| F | ⊙ I don't feel I am being punished<br>○ I feel I may be punished<br>○ I expect to be punished<br>○ I feel I am being punished |

FIG.6

[Close Without Saving] [Save and Mark Complete] [Save and Mark Incomplete]

Questionnaire Section Five for jacob e6 teitelbaum
Yeast Questionnaire
Use TAB key to move the cursor to the next question.

The score for this section of the questionnaire gives us the probability of yeast overgrowth being a significant factor in your case.

Patient Total:          270.0

SECTION A: YOUR MEDICAL HISTORY

| |
|---|
| Have you been treated for acne with tetracycline, erythromycin, or any other antibiotic for one month or longer?<br>⊙ Yes<br>○ No |
| Have you taken antibiotics for any type of infection for more than two consecutive months, or in shorter courses four or more times in a twelve-month period?<br>⊙ Yes<br>○ No |
| Have you ever taken an antibiotic-even for a single course?<br>⊙ Yes<br>○ No |
| Have you ever had prostatitis, vaginitis, or another infection or problem with your reproductive organs for more than one month?<br>⊙ Yes<br>○ No |
| Have you ever been pregnant:<br>○ Two or more times<br>○ Once<br>⊙ Never |
| Have you taken birth control pills for:<br>○ More than two years<br>○ Six months to two years<br>⊙ Never |
| Have you taken corticosteroids such as Prednisone, Cortef, or Medrol by mouth or inhaler for:<br>⊙ More than two weeks<br>○ Two weeks or less<br>○ Never |

FIG.7

[📄 Close Without Saving]  [💾 Save and Mark Complete]  [💾 Save and Mark Incomplete]

Questionnaire Section Six for jacob e6 teitelbaum

Use TAB key to move the cursor to the next question.

Lab Values

Reporting Your lab Values
We're almost done!

For the labs in the first section (in blue), enter the results for ALL the tests (or check the "not done" box). When requested, put in the "normal range" values (they are in the lab sheet, often after, above or below the result). Please enter just the number results (not the letters/units that come after it).

For all other labs (section two-in black), only enter the results and normal range if your lab test is abnormal. This is usually marked to make it stand out for your doctor.

We have tried to make this as straightforward as possible. If you like, however you can mail or fax us your labs to our office and, for a $30 fee, one of our staff will enter the pertinent results onto your program and e-mail (or write) you when this is done. If you would like to do this, click here for a form to attach to your labs. We will bill your credit card for the $30 fee. Be sure to attach this form to your labs.

Section 1
*(for this section, add your result whether it is normal or abnormal).*

| Tests Done? | Test Name | Your Results | Normal Range |
|---|---|---|---|
| ☑ Section Complete | | | |
| ☐ Not Done | ESR (Sed Rate or Sedimentation Rate) | 5 | Not Needed |
| ☐ Not Done | Free T4 (Free Thyroxine) | 0.7 | 0.7 to 2 |
| ☑ Not Done | Total T3 (Triiodothyronine) | | to |
| ☑ Not Done | Free T4 or T7 index | | to |
| ☐ Not Done | TSH (Thyroid Stimulation Hormone) | 0.5 | Not Needed |
| ☐ Not Done | DHEA-S (DHEA-Sulphate) <br> What units are these results measured in? <br> ⊙ Mcg/dL <br> ○ UmoL/L <br> ○ None of these | 111 | Optimum Range <br> *Males* <br> 325-480 mcg/DL <br> 8.7-12.6 uMOL/L <br> *Females* <br> 140-180 mcg/DL <br> 3.8-4.6 uMOL/L |
| ☐ Not Done | B12 Level (Vitamin) | 287 | Not Needed |

FIG.8
WEB SITE DIAGNOSIS LIST

A. Hypothyroidism (*print* "Low Thyroid" *sheets*)-* *If TSH is under 4.0 and T4 and T3 test within the normal range put " - subclinical" after "Hypothyroidism".*
B. Inadequate Adrenal Function (*print* "Low Cortisol", "Ginsing" & "Licorice" *sheets*)-* *If 1st Cortisol is over 6 and, if available, 2nd and 3rd Cortisol are more than 7 and 11 points greater than 1st Cortisol or if 1st Cortisol is over 16, put "-subclinical" after "function". If no Cortisol level done put "suspected" before "Inadequate"*
C. Suboptimal DHEA Level (*print* "Low DHEA" & "Low Cortisol" *sheets*)
D. Suboptimal Estrogen Levels *(print "Low Estrogen" sheet in females only)-Mosh-Females only, do NOT use this diagnosis for males.*
E. Testosterone Deficiency *(print* "Low Testosterone" & "Low Estrogen" *sheet).* - *If Free testosterone is not below the bottom number in the "normal range" put "-subclinical"*
F. Suspected Fungal Overgrowth - *(print* "Yeast Infection" *sheet).*
G. Suspected Cipro or Doxycycline Sensitive Occult Infection (e.g. Mycoplasma Incognitus, Chlamydia) or Viral Infection - *(print* "Hidden Infections" *sheet).*
H. Rule out Polymyalgia Rheumatica.
I. Elevated Sed rate-Etiology? - *Print* "Elevated Sed Rate" *sheet). (Mosh-if this is printed, put "ESR=[result of ESR lab #3 after the word "etiology"])*
J. Rule out Lymes -
K. Elevated ANA - Rule out Lupus -
L. Elevated Latex Fixation - Rule out Rheumatoid Arthritis
M. Elevated Prolactin - Likely from CFIDS/FMS associated hypothalamic dysfunction - if elevation persists, rule out pituitary Adenoma or caused by medication (e.g., Risperdol).
N. Possible Oxytocin deficiency - *(print* "Oxytocin" *sections from newsletter issue #5).*
O. Rule out Prostatitis/Urethritis - *(print* "Prostatitis" *sheet).* Never use this diagnosis in females!
Q. Rule out Sleep Apnea - *(print* "Sleep Apnea" *sheet).*
R. Disordered Sleep - *(print* "Poor Sleep" *sheet).*
S. Hyperthyroidism *(If T3 and T4 both below upper limit of normal add "subclinical").*
T. Rule out elevated Cortisol
U. Rule out Bowel Bacteria Overgrowth or Parasite. (Print parasite sheet)
V. NMH-Neurally Mediated Hypotension *(If no Tilt test done, add "-suspected" and print* "NMH" *sheet).*
W. Chronic Rhinitis/Sinusitis/Nasal Congestion - *(print* "Nasal Congestion" *sheet).*
X. Rule out Ciguetara (Fish Toxin) Poisoning
Y. Restless Leg Syndrome suspected - *(print* "Restless Leg Syndrome" *sheet).*
Z. Codeine Responsive Fatigue
AA. Possible Depression - always list this as the last diagnosis in the section it's in (e.g., most likely diagnosis or suspected diagnosis)
BB. Seasonal Affective Disorder-print out information sheet

*(If diagnosis A & S both printed, put them on the same line [e.g., both as diagnosis #"x"] and put "rule out" before both and "see labs and review Thyroid Rx and clinical symptoms" after 2nd diagnosis [e.g., #4- "rule out subclinical hyperthyroidism; rule out hypothyroidism; see labs and review any thyroid Rx and clinical symptoms")*

AUTOMATED QUESTIONNAIRE FOR ASSISTING IN THE DIAGNOSIS AND TREATMENT OF MEDICAL PROBLEMS AND FOR DATA GATHERING, ANALYSIS AND ORGANIZATION TO MAKE A COMPLETE MEDICAL HISTORY AND ILLNESS RECORD

BACKGROUND OF THE INVENTION

1. Field of the Invention

The present invention is drawn to an automated questioner for assisting in the diagnosis and treatment of medical problems. In one particular embodiment, the invention diagnoses and creates a treatment plan for Fibromyalgia and Chronic Fatigue Syndrome. In addition, it elicits, analyzes and organizes the patient's medical history, symptoms and lab results to make a complete medical history and illness record in medical record format.

2. Description of Related Art

Medicine is a rapidly changing field that changes faster than doctors can learn. Also, the time a doctor has for each patient has decreased to an average visit of 8 minutes. Both of these factors compromise a doctor's ability to properly care for patients.

One example is the treatment of Fibromyalgia (FMS). Fibromyalgia, which currently affects an estimated 3 to 6 million Americans, and Chronic Fatigue Syndrome (CFS) are two illnesses which often coexist. Severe persistent fatigue, diffuse migratory pain, cognitive dysfunction, and disordered sleep are common symptoms that patients often report in these overlapping syndromes. Current hypotheses suggest that many triggers can initiate a cascade of events, causing hypothalamic dysfunction and associated loss of normal circadian cycling. This may result in some of the changes reported in FMS and/or CFS. These include:

1. Disordered sleep with associated pain. Disordered sleep (as well as hormonal and other changes) may cause immune dysfunction ( e.g., Natural Killer Cell dysfunction and decreased proliferate responses and opportunistic infections).
2. Hormonal deficiencies and hypothalamic-pituitary-target gland axis dysfunction. These can also contribute to the neurotransmitter changes seen in FMS.
3. Autonomic dysfunction—including Neurally Mediated Hypotension (NMH).

Some authors have also suspected macro and micro nutrient deficiencies. In an initial pilot study and a subsequent placebo-controlled study, it was found that simultaneously treating the above problems resulted in significant clinical improvement. Which mix of treatments was needed, however, varied from patient to patient.

Although a concept that is sometimes uncomfortable and foreign to our way of thinking, the need for multiple interventions can occur when an illness affects a critical control center (such as the hypothalamus) that impacts the multiple systems noted above. A single treatment that reverses the hypothalamic dysfunction directly has not yet been found. Thus, this situation is different from illnesses that affect a single target organ, which can be treated with a single treatment. For example, the pituitary dysfunction itself often requires treatment with many treatments simultaneously and hypothalamic dysfunction disables several critical systems in addition to the pituitary gland. It has therefore been found that an integrated treatment approach based on simultaneously treating the above problems, even if a modest degree of suspicion is present, will be clinically beneficial in FMS.

Although a complex treatment protocol, it has been found that this integrated approach will assist in proper diagnosis and treatment plans. Unlike previous diagnosis and treatment plans, the present invention does not merely seek to find the cause of and cure for symptoms. Instead, the present invention analyzes symptoms and lab tests to identify the root causes of the problems causing the symptoms and to enable an effective treatment protocol to be determined for each patient. As discussed above, this may not come from a single source but may have many different causes. The present invention evaluates for each of the causes and creates an effective treatment plan. In particular the present invention (1) evaluates Fibromyalgia and Chronic Fatigue Syndrome, and creates an effective treatment plan to find the root causes of the symptoms and provide a remedy for each root cause resulting in an effective treatment, (2) acts as a computerized physician to elicit and analyze a thorough patient medical history and lab tests, thereby determining the diagnosis for overall day to day medical problems, determining what further tests are needed and creates a medical record for any sick or healthy patient.

SUMMARY OF THE INVENTION

The present invention is an automated questionnaire for assisting in the diagnosis and treatment of medical problems of a patient. The questionnaire has a basic symptom module that gathers basic symptom information of the patient and assigns point values to the basic symptom information. A systems review module gathers system information of the patient and assigns point values to the system information and a diagnosis module that evaluates the basic symptom information point values and the system information point values to determine a possible diagnosis.

The present invention is also a method for assisting in the diagnosis and treatment of medical problems of a patient. The method has the steps of gathering basic symptom information of the patient and assigning point values to the basic symptom information, gathering system information of the patient and assigning point values to the system information, and evaluating the basic symptom information point values and the system information point values to determine a possible diagnosis.

BRIEF DESCRIPTION OF THE DRAWINGS

The objects and features of the invention will be more readily understood with reference to the following description and the attached drawings.

FIG. 2 is an illustration of a screen showing questions asked in section one of the questionnaire.

FIG. 3 is an illustration of a screen showing questions asked in section two of the questionnaire.

FIG. 4 is an illustration of a screen showing questions asked in section three of the questionnaire.

FIG. 5 is an illustration of a screen showing questions asked in section four of the questionnaire.

FIG. 6 is an illustration of a screen showing questions asked in section five of the questionnaire.

FIG. 7 is an illustration of a screen showing questions asked in the lab section of the questionnaire.

FIG. 8 is a list of diagnoses in one embodiment of the invention.

DETAILED DESCRIPTION

Figure 1:
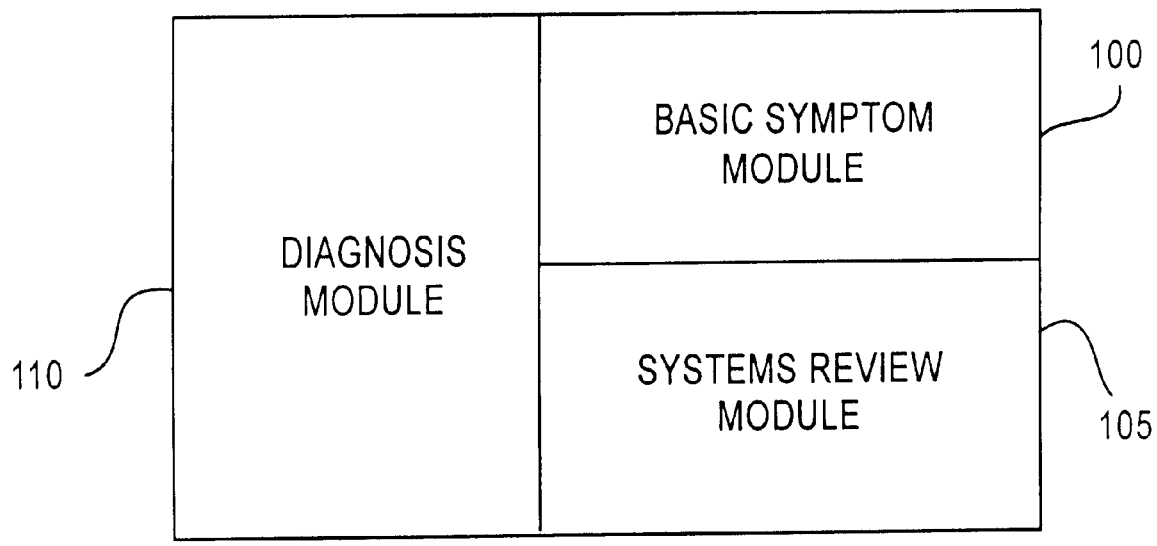
FIG. 1 is a general block diagram of an automated questionnaire for assisting in the diagnosis and treatment of medical problems.

The invention of the present application is an automated questionnaire for assisting in the diagnosis and treatment of overall medical problems of a patient. One embodiment of the invention applies a newly discovered and proven treatment and diagnostic protocol/program for Chronic Fatigue Syndrome and Fibromyalgia. FIG. 1 is an illustration of an embodiment of the invention having a basic symptom module 100 that gathers basic symptom information of a patient and assigns point values to the basic symptom information.

For example the basic symptom module 100 may be part of a computer program, that queries the patient with regard to basic symptoms the patient is experiencing. Some examples of questions that may be asked are:

1) How long have you been fatigued?
2) What was the approximate date or time of onset?
3) How much fatigue decreased your function?
4) Did the symptoms begin suddenly or gradually?

All of the above questions will be used in making a diagnosis. Although all four questions will be used in making a diagnosis or diagnoses, only question 4 will be given a point value, which will assist in making a diagnosis.

In one embodiment of the invention there are 27 diagnoses A–O, Q–Z, AA and BB, which contribute to causing CFS and FMS. The diagnoses are as follows:

A. Hypothyroidism
B. Inadequate Adrenal Function
C. Suboptimal DHEA Level
D. Suboptimal Estrogen Levels
E. Testosterone Deficiency
F. Suspected Cipro or Doxycycline Sensitive Occult Infection
G. Suspected Fungal Overgrowth
H. Rule out Polymyalgia Rheumatica
I. Elevated Sed Rate
J. Rule out Lymes
K. Elevated ANA—Rule out Lupus
L. Elevated Latex Fixation
M. Elevated Prolactin
N. Possible Oxytocin Deficiency
O. Rule out Prostatitis/Urethritis
Q. Rule out Sleep Apnea
R. Disordered Sleep
S. Hyperthyroidism
T. Rule out Elevated Cortisol
U. Rule out Bowel Bacteria Overgrowth of Parasite
V. NMH—Neurally Mediated Hypotension
W. Chronic Rhinitis/Sinusitis/Nasal Congestion
X. Rule out Ciguetara (Fish Toxin) Poisoning
Y. Restless Leg Syndrome suspected
Z. Codeine Responsive Fatigue
AA. Possible Depression
BB. Seasonal Affective Disorder If the patient answers question 4 by stating that the symptoms occurred suddenly, 10 points will be added to diagnosis B. As the patient answers questions, points are assigned to each diagnosis accordingly. Once the point value of a diagnosis reaches a specific level, the diagnosis will be considered as a possible and at a higher score a probable cause of the patient's symptoms.

In the event that no point values are given to a particular answer to a question, the answer will still be used to assist in diagnosing the patient. For example, the answers to questions 1–3 will be provided to a physician as general background information for consideration when diagnosing a patient. In one embodiment of the invention a diagnosis will be made after analyzing the data using a yes/no decision tree to determine a probable diagnosis.

In some instances, a combination of answers to the questions may be provided to a physician in a more usable manner. For instance, question 4 asks whether the symptoms occurred suddenly or gradually. A question later asked by the Basic Symptom Module 100 is whether the symptoms occurred after pregnancy or after an accident. If the symptoms occurred after pregnancy or after an accident more explicit details will be requested. The physician in this case will be alerted of both answers at one time in the following format:

Onset: answer to question 5 and answer to 137.

If the answer to question 5 is suddenly and the answer to question 137 is immediately after a car accident, the physician will be alerted of both answers at one time as follows:

Onset: Suddenly, immediately after a car accident.

In essence the questionnaire asks questions in a logical order for the patient to answer and then reports the answers to the physician in a logical way so that the physician can better assess and diagnose the patient's symptoms.

The questionnaire also has a Systems Review Module 105 to assist in diagnosing a patient's symptoms. The Systems Review Module 105 asks the patient questions regarding symptoms the patient is experiencing in relation to the patient's systems. For example, in one embodiment the patient is asked questions regarding symptoms relating to systems using an Adrenal Checklist, Thyroid Checklist, Other Hormones, Vasodepressor Syncope (NMH), Lymes, Prostatitis, Sinusitis/Nasal Congestion & Other Infections, Disordered Sleep, Seasonal Affective Disorder, Yeast Overgrowth, Parasites and Vision/Dental. The reason that the questions are broken up into systems is that most symptoms are caused by a malfunction of one or more of these systems.

In the past, the patient may have been asked some of the same questions as asked in questionnaire of the present invention. However, the answers to the questions were not analyzed correctly because physicians concentrated on curing the symptom without looking to the root of the problem.

One analogy that illustrates this point concerns a car owner who was having electrical system problems with his car. The owner of the car went to the garage and complained that the car had the following symptoms: the car will not start, the radio will not play and the headlights will not turn on. A mechanic at the shop evaluated the symptoms and decided that there must be some type electrical problem. The mechanic decided to check the battery and found that the battery was dead. In order to cure the symptoms the mechanic changed the battery and everything worked fine. The car started on the first try, the radio played music and the lights illuminated the road.

One year later the owner of the car came in with the car and complained that the car was suffering the same symptoms. The car would not start, the radio would not play and the headlights would not turn on. Again the mechanic decided to change the battery and the symptoms went away. However, every year the car owner came back with the same symptoms and the mechanic provided the same solution.

Finally the car owner grew tired of bringing the car back to the mechanic and decided to try a new mechanic. The car owner told the new mechanic the symptoms the car was experiencing. The car would not start, the radio would not play and the headlights would not turn on. Like the last mechanic, the new mechanic decided that there was some type of electrical problem. The new mechanic like the old mechanic checked the battery and found that it was dead. However unlike the old mechanic the new mechanic did not want to just change the battery to temporarily cure the symptoms but looked to the root of the problem. The new mechanic remembered that the alternator charged the battery and kept the battery from dying. Therefore the new mechanic checked the alternator, the root of the problem, and found that it was faulty. The new mechanic in addition to replacing the battery also replaced the alternator. From then on the car owner has not had any electrical problems with the car.

From the above it is evident that the new mechanic cured the symptoms that the car was experiencing by going to the root of the problem and changing the alternator. Likewise the questionnaire asks questions through the Systems Review Module 105 regarding the patients systems, which will help the physician, identify the root of the patient's symptoms in order to cure the patient.

Also assisting the physician in diagnosing a patient's symptoms is a Diagnosis Module 110. The Diagnosis Module 110 evaluates the answers obtained from Basic Symptom Module 100 and Systems Review Module 105 to assist the physician in diagnosing the symptoms of the patient. In one embodiment of the invention the Diagnosis Module 110 assigns point values to each of the answers. The point values will be added to one or more of the possible diagnoses. If a particular diagnosis reaches a certain threshold number of points the diagnosis will be listed as a possible cause of the symptoms. In another embodiment of the invention the Diagnosis Module 110 will produce a formatting document which will put all the answers obtained from Basic Symptom Module 100 and Systems Review Module 105 into a form that will allow a physician to more easily analyze and diagnose a patient's symptoms.

In one embodiment of the invention the questionnaire is made up of six basic sections. The first section is directed to questions relating to background information of a patient such as name, address, birth date etc. The second section is directed to questions regarding what types of drugs a patient has taken, for what reason the drugs were taken and types of reactions the patient has had to the drugs. The third section is a symptom checklist, which not only asks questions with regard to present symptoms the patient is experiencing but also asks questions regarding past illnesses and symptoms. The fourth section asks questions regarding a patient's psychological profile. In one embodiment of the invention a Beck Inventory is taken in order to get a patient's psychological profile. The fifth section is directed to questions regarding fungi and yeast. It has been found that infections with fungi and yeast may be a contributing factor to Fibromyalgia and Chronic Fatigue Syndrome. Finally, the sixth section is provided so that if lab results are available, the lab results can be used in assisting in the diagnosis and treatment of a patient.

Once all the questions of the questionnaire have been answered, the answers will be converted into a more readable form. In one embodiment of the invention the answers to the questions will be placed in a Formatting Document that not only puts the answers to the questions in the organized and readable form needed in modem medicine but also creates a diagnosis list and possible treatments based on the answers given. In general the questionnaire looks for major underlying causes of the symptoms the patient is experiencing and defines therapies and interventions needed. The questionnaire also gives the patient and physician detailed information on what types of treatments they should try and what they need to know to understand the diagnosis and treatments and how to use the treatments safely and effectively thereby educating the patient.

One embodiment of the invention is a questionnaire for diagnosing Fibromyalgia and Chronic Fatigue Syndrome. In this embodiment of the invention, the questionnaire shown in Appendix A and incorporated by reference hereunder is made up of 6 sections and asks questions that will specifically help determine a diagnosis and create a treatment plan for someone suffering from Fibromyalgia or Chronic Fatigue Syndrome.

FIG. 2 is an illustration of the types of questions the patient will be asked in the first section of the questionnaire. The first section of the questionnaire will ask for general contact information such as the patient's name, address and phone number. Section 1 will then go on to ask for general symptoms the patient is experiencing such as:

How long have you been fatigued?

What was the approximate date or time of onset?

How much has fatigue decreased your function?

Did the symptoms begin_____suddenly or _____gradually?

ETC.

Section 1 also will ask the patient about their past medical history. Some questions that are asked are:

Do you have Emphysema?

Do you have Hypertension?

Do you have Asthma?

Do you Stomach Ulcers?

ETC.

In general section 1 asks the patient for basic contact information, basic symptoms the patient is experiencing and past medical history.

FIG. 3 is an illustration of the types of questions the patient will be asked in the second section of the questionnaire. In general the questionnaire will ask:

What types of medication the patient has taken in the past?

Were there any allergic or prohibitive side effects?

How effective is the medication?

When did the patient stop taking the medicine?

Why was the medicine discontinued?

What is the current dosage of medicine being taken?

What other types of treatment are you taking?

What types of non-prescription treatments are you taking?

FIG. 4 is an illustration of the types of questions the patient will be asked in section 3 of the questionnaire. This section initially asks questions relating to common symptoms of Chronic Fatigue Syndrome or Fibromyalgia criteria. Some of the relevant questions asked relate to how the patient generally feels at the present time and how long the patient has been experiencing the symptoms.

Section 3 of the questionnaire also breaks down the questions into systems checklists. In general the questionnaire is broken down into the following systems checklists:

Adrenal Checklist

Thyroid Checklist

Other Hormones
Vasodepressor Syncope (NMH)
Lymes
Prostatitis (males only)
Sinusitis/Nasal Congestion & Other Infections
Disordered Sleep
Seasonal Affective Disorder
Yeast Overgrowth
Parasites
Vision/Dental
Other Problems and Questions As stated previously, answers to the questions are assigned point values that will be used in diagnosing a patient. The bulk of the questions that are used in diagnosing a patient are found in section three thru six of the questionnaire, which is the symptoms checklist.

Section three of the questionnaire is broken up into systems checklists in an effort to find the root of the problem. Specifically, the questions are organized in such a way to find the root of the problem instead of trying to find general control center causes. In the case of a patient suffering from Chronic Fatigue Syndrome or Fibromyalgia the questions are more specifically directed to find how the hypothalmic gland is being affected. Hypothalmic gland dysfunction has been found to be an underlying cause of Chronic Fatigue Syndrome and Fibromyalgia. By determining how these symptoms or systems affect and are affected by the hypothalmus, proper treatment of Chronic Fatigue Syndrome or Fibromyalgia can be accomplished.

FIG. 5 is an illustration of questions asked in section four of the questionnaire. The questions asked in section four of the questionnaire are directed to the psychology of the patient. In short section four of the questionnaire makes a psychiatric evaluation of the patient.

In one embodiment of the invention, the psychological profile of the patient is taken through the use of the Beck Inventory. The Beck Inventory is a series of questions designed to make an accurate assessment of a patient's psychology. In this section points are tallied answers to each questions and added to the corresponding diagnosis.

FIG. 6 is an illustration of questions the patient will be queried in section five of the questionnaire. In particular this section is a yeast questionnaire. It has been found that one significant factor in the cause of Fibromyalgia and Chronic Fatigue Syndrome can be the exposure to fungus and more particularly yeast.

Finally, FIG. 7 is an illustration of questions a patient is queried by the questionnaire regarding lab values. This section will highlight significant lab values which attribute to the cause of symptoms the patient is experiencing, and analyzes lab values to determine underlying diagnoses. Certain tests results are highlighted as important, normal and abnormal.

FIG. 8 is a list of diagnoses that may be contributed to a patient's Fibromyalgia and Chronic Fatigue Syndrome. From the answers provided by the patient, each answer is given a point value and added to the diagnosis list. For example, if the patient answers the following question from the adrenal checklist as yes, "do you have sugar cravings?" 20 points will be added to diagnosis B.

A final analysis is then generated after all the questions have been answered and the answers have been analyzed. In the final analysis as shown in Appendix B and incorporated by reference hereunder, the points for each diagnosis are tallied. If the point value for a diagnosis is greater than 150 the diagnosis is deemed as "most likely". If the point value for a diagnosis is greater than 80 but less than 150 the diagnosis is deemed as probable.

A final report is then generated after the final analysis made. The final report is made up of three parts. The first and third parts (information sheets) are for the patient and the second part is for the patient's physician.

The first part of the final report for the patient includes a cover letter, an assessment of the patient's symptoms, recommendations, a treatment protocol for determining how to treat the patients symptoms, flowcharts for prescription and non-prescription drugs and other relevant and useful information on how to treat the patients symptoms. It also highlights for the patient critical problems that must be evaluated (e.g. breast lumps). A supplies page is also provided so that the patient will have access to the necessary supplies needed for treatment.

The second part of the final report or formatting document for the physician has many sections. The first section is a letter highlighting major problems that require attention (e.g. angina, breast lumps, rectal bleeding).

This is included in an introductory cover page in which Dr. Teitelbaum is introduced as the physician who created the questionnaire and reference materials that are helpful in treating the patient's symptoms are made available to the physician.

The second section includes the many parts that comprise a complete medical record including (but not limited to):

1) A core database which allows a quick overview of the patient's medical history and treatments.
2) A detailed history of present illness.
3) Review of systems that addresses and evaluates the patients symptoms.
4) Pages 7 and 8 show the patients past medical history. The type of information revealed in this section are past diagnoses and dates, past operations and dates, past hospitalizations, reasons for hospitalizations and dates, medications taken, allergies, sensitivities, current medications being taken, current treatments, previous treatments, prescription drugs being taken and non-prescription drugs being taken.
5) Page 9 shows the family history of the patient.
6) Page 10 is a social history of the patient. This section includes martial status, information regarding the patient's spouse, number of years married, number of children, types of foods consumed by the patient, activities, habits and life stresses the patient is experiencing.
7) Page 11 has information relating to the results of a physical exam of the patient. This section may be left blank if no physical exam has been done or the values and results may be filled in if a physical exam has been done.
8) Page 12 has information regarding lab values. All relevant information regarding the patient's lab values is provided in this section.
9) Page 13 is a detailed assessment of the patient's condition. This section provides a diagnosis or diagnoses, suspected contributing or associated factors and other diagnoses.
10) Page 14 is a list of recommendations of how to treat and further evaluate the patient. Included in this section are a list of prescription therapies, needed tests, non-prescription therapies, a treatment protocol and a flow chart of types of treatments the patient should undergo including prescription and non-prescription treatments.

11) Page 16 is a treatment protocol listing recommended treatments and options and suggestions for future treatments should they be needed.

12) Page 18 discusses the cover letter to the patient discussing the patient's diagnoses, causes and treatment plan. This section also provides general information discussing the diagnoses, general causes and basics in keeping the body healthy and strong.

The present invention in one embodiment is a method of diagnosing and treating a patient. This method can be implemented as a computer program. The computer program can be implemented as a stand-alone system or could be part of a network. In order to reach more people the computer program could be available over a public network such as the Internet or could be made available to a select group of people over an intranet.

In one embodiment of the invention a user registers. The user inputs their name, phone number, email address, password and optionally their address. The user then can log into the questionnaire.

Initially the user enters basic information such as their name, email address and optionally their address. Billing information is then entered which could be third party insurance information.

The user then proceeds to fill out section 1 of the questionnaire. First basic detailed information such as main symptoms, date of onset, age and number of children is inputted. Second the users medical history is inputted. Information such as diagnoses and dates, and operations and dates are requested.

In section two of the questionnaire, the user enters current/past medications, doses and effects.

In section three of the questionnaire the user is asked questions regarding basic symptoms meeting Chronic Fatigue Syndrome or Fibromyalgia criteria and how the patient is generally feeling. Section three also includes a systems review regarding the patient's current condition and past condition falling under major diagnoses categories.

Section four the questionnaire asks general questions relating to the psychology of the patients. In this particular embodiment of the invention, a Beck Inventory is taken to determine the psychological profile of the patient. This section also determines the possibility of fish poisoning through the use of a pain summary.

Section five of the questionnaire is a yeast inventory determining whether the patient symptoms are caused from infections with mold or yeast.

Section six of the questionnaire, which is an optional section, provides a place for lab values to be entered. This section highlights certain tests that are determined as being important in the diagnosis of the patient's symptoms. In certain circumstances, normal and abnormal lab results are highlighted. In other circumstances, only abnormal lab results are highlighted.

A final analysis is provided diagnosing the patient's symptoms. Each diagnosis is given a numerical value based on the answers given for each question of the questionnaire. In one specific embodiment of the invention, a score of 150 or greater will deem the diagnosis as being most likely. A score of between 80 and 150 will deem the diagnosis as being probable A final report is provided for the patients including a cover letter, assessment, recommendation, flow charts and other useful information.

A final report for the physician is also provided that includes a cover letter, core database, medical record, HOPI, symptom breakdown, review of systems, past medical history, family history, social history, physical exam, lab values, assessment, treatment protocol, flow charts, and other useful information.

Finally, information sheets are provided as further information regarding the diagnoses and treatment.

Although the invention has been described based upon the embodiments discussed above, it would be apparent to those skilled in the art that certain modifications, variations and alternative constructions would be apparent, while remaining within the spirit and scope of the invention.

I claim:

1. An automated questionnaire for assisting in the diagnosis and treatment of medical problems of a patient comprising:

a basic symptom module that gathers basic symptom information of the patient and assigns point values to the basic symptom information;

a systems review module that gathers system information of the patient and assigns point values to the system information; and a diagnosis module that evaluates the basic symptom information point values and the system information point values to determine a diagnosis.

2. The automated questionnaire as claimed in claim 1 further comprising:

a medical history module that gathers medical history information of the patient;

a formatting module that places the basic symptom information, the medical history information and the possible diagnosis into an organized and readable form for evaluation.

3. The automated questionnaire as claimed in claim 1 wherein said basic symptom module asks basic background questions, drugs a patient has taken, psychological questions and questions regarding the patient's exposure to mold.

4. The automated questionnaire as claimed in claim 1 wherein said systems review module comprises of questions split up into the following systems groups:

Adrenal Checklist

Thyroid Checklist

Other Hormones

Vasodepressor Syncope (NMH)

Lymes

Prostatitis

Sinusitis/Nasal Congestion

Other Infections

Disordered Sleep

Seasonal Affective Disorder

Yeast Overgrowth

Parasites

Vision/Dental.

5. The automated questionnaire as claimed in claim 1 wherein said diagnosis module adds said basic symptom information point values and said system information point values to make a diagnosis value for each diagnosis.

6. The automated questionnaire as claimed in claim 5 wherein when said diagnosis value reaches a threshold said diagnosis is deemed a diagnosis.

7. The automated questionnaire as claimed in claim 6 wherein when said diagnosis value is greater than 80 but less than 150 said diagnosis is deemed as probable.

8. The automated questionnaire as recited in claim 6 wherein when said diagnosis value is greater than 150 said diagnosis is deemed as most likely.

9. A method for assisting in the diagnosis and treatment of medical problems of a patient comprising the steps of:

gathering basic symptom information of the patient and assigning point values to the basic symptom information;

gathering system information of the patient and assigning point values to the system information; and evaluating the basic symptom information point values and the system information point values to determine a possible diagnosis.

10. The method as claimed in claim 9 further comprising the steps of:

gathering medical history information of the patient; and organizing the basic symptom information, the medical history information and the possible diagnosis into an organized and readable form for evaluation.

11. The method as claimed in claim 9 wherein said step of gathering basic symptom information further comprises the step of gathering information regarding basic background questions, drugs a patient has taken, psychological questions and questions regarding the patient's exposure to mold.

12. The method as claimed in claim 9 wherein said step of gathering system information further comprises the step of gathering information in the following systems groups:

Adrenal Checklist

Thyroid Checklist

Other Hormones

Vasodepressor Syncope (NMH)

Lymes

Prostatitis

Sinusitis/Nasal Congestion

Other Infections

Disordered Sleep

Seasonal Affective Disorder

Yeast Overgrowth

Parasites

Vision/Dental.

13. The method as claimed in claim 9 wherein said step of evaluating said basic symptom point values and said system information point values further comprises the step of adding said basic symptom information point values and said system information point values to make a diagnosis value for each diagnosis.

14. The method as claimed in claim 13 further comprising the step of diagnosing the patient when said diagnosis value reaches a threshold.

15. The method as claimed in claim 14 further comprising the step of making a probable diagnosis when said diagnosis value is greater than 80 but less than 150.

16. The method as claimed in claim 14 further comprising the step of making a most likely diagnosis when said diagnosis value is greater than 150.

17. The method as claimed in claim 9 further comprising the step of using a computerized decision tree algorithm to elicit and or evaluate symptom and systems information to determine probable diagnoses and or further testing needs.

* * * * *